United States Patent [19]

Steinmetz et al.

[11] Patent Number: 4,780,563

[45] Date of Patent: Oct. 25, 1988

[54] PROCESS FOR THE CO-PRODUCTION OF AROMATIC CARBOXYLATES AND ALKYL IODIDES

[75] Inventors: Guy R. Steinmetz; Mark Rule; Victor H. Agreda; Lanney C. Treece, all of Kingsport, Tenn.

[73] Assignee: Eastman Kodak Company, Rochester, N.Y.

[21] Appl. No.: 109,974

[22] Filed: Oct. 19, 1987

[51] Int. Cl.$^4$ .................... C07C 67/36; C07C 17/00
[52] U.S. Cl. .................................... 560/80; 560/97; 560/100; 560/102; 560/103; 570/181
[58] Field of Search .................. 570/181; 560/97, 100, 560/80, 102, 103

[56] References Cited

U.S. PATENT DOCUMENTS

| | | | |
|---|---|---|---|
| 2,565,462 | 8/1951 | Prichard et al. | 560/97 |
| 2,565,464 | 8/1951 | Tabet | 560/97 |
| 3,988,358 | 10/1976 | Heck | 560/97 X |

Primary Examiner—Werren B. Lone
Assistant Examiner—Vera C. Clarke
Attorney, Agent, or Firm—Charles R. Martin; William P. Heath, Jr.

[57] ABSTRACT

Disclosed is a process for the co-production of aromatic carboxylic esters and alkyl iodides by the carbonylation of aromatic iodides in the presence of an ether and a palladium catalyst.

12 Claims, No Drawings

PROCESS FOR THE CO-PRODUCTION OF AROMATIC CARBOXYLATES AND ALKYL IODIDES

This invention relates to a novel carbonylation process for the preparation of both aromatic carboxylic esters with low acid content and an iodine containing compound from which the iodine values can be economically recovered. The carbonylation is conducted in the presence of an ether and a catalytic amount of palladium.

The carbonylation of aromatic halides in the presence of palladium to obtain aromatic carboxylic acids and esters is well known in the art. U.S. Pat. No. 3,988,358 discloses the carbonylation of aromatic halides in the presence of an alcohol and a tertiary amine to produce the corresponding carboxylic acid ester.

While it is known that aromatic iodides can be carbonylated, the use of these materials has been discouraged by the cost associated with the difficulty of recovering the iodine values. For example, the use of basic materials in the carbonylation of aromatic halides, such as tri-n-butyl amine in U.S. Pat. No. 3,988,358, results in the formation of halide salts from which the halide values can be reclaimed only through uneconomical procedures involving severe chemical treatments.

In U.S. Pat. No. 2,565,462, Prichard and Tabet disclose the carbonylation of aromatic halides to aromatic esters in the presence of alcohols, ethers, and phenols using nickel tetracarbonyl. However, only noncatalytic quantities of iron, nickel, and cobalt are used as promoters under reaction conditions of both temperature and pressure that are much more severe than is shown by our invention.

U.S. application Ser. No. 922,574 discloses the carbonylation of aromatic halides to aromatic carboxylic esters and alkyl iodines in the presence of an alkanol and palladium. When alcohols are employed in reactions under typical carbonylation reaction conditions for aryl halides, water is a byproduct. Water can be formed in a number of different ways. For example, reaction of in situ generated hydrogen iodide with methanol results in the formation of methyl iodide and water. Alcohols can often dehydrate to their corresponding ether and water under typical carbonylation reaction conditions. The presence of water in the reaction mixture often leads to the production of a mixture of both carboxylic acids and esters. The presence of acid groups can present a purification problem if pure ester is desired as a polymer precursor.

We have discovered a process which not only results in the carbonylation of aromatic iodides to aromatic carboxylic esters with low acid content in excellent yields and at excellent rates of conversion but also results in production of alkyl iodides from which the iodine values can be economically recovered. In this invention the carbonylation is conducted in the presence of an ether and a catalytic amount of a palladium catalyst under aromatic carboxylic ester and alkyl iodide-forming conditions of temperature and pressure.

The advantage afforded by our invention over the prior art is two-fold. First, the iodine values in the alkyl iodide may be readily recovered by simply flashing the relatively volatile alkyl iodide from the mixture resulting from the carbonylation reaction. This can be accomplished either in the carbonylation reactor or, more preferably, in a pressure reduction vessel to which the mixture resulting from the carbonylation reaction is fed. Second, the object in feeding organic ethers is to minimize the amount of water in the carbonylation reactor which will reduce the acid content of the ester product. The ratio of aromatic esters to acids produced in the present invention is dependent on the concentration of water present in the carbonylation reactor. The capability of producing aromatic carboxylic esters with low acid content is both novel and useful. The low acid content allows for simpler and less expensive production and purification schemes and eliminates the need for an esterification step when esters are the desired product.

The aromatic iodides which may be used in our process may be monoiodo or polyiodo, e.g. di-, tri- and tetra-iodo aromatic compounds. The aromatic nucleus or moiety can contain from 6 to 18 carbon atoms, preferably 6 to 10 carbon atoms and may be carbocyclic aromatic such as benzene, biphenyl, terphenyl, naphthalene, anthracene, etc., or heterocyclic aromatic such as pyridine, thiophene, pyrrole, indole, etc. In addition to one or more iodine atoms, the aromatic moiety may be substituted by various substituents inert under the conditions employed in our process. Examples of such substituents include alkyl of up to about 12 carbon atoms such as methyl, ethyl, isobutyl, hexyl, 2-ethylhexyl, nonyl, decyl, dodecyl, etc.; cycloalkyl of about 5 to 12 carbon atoms such as cyclopentyl, cyclohexyl, 4-butylcyclohexyl, etc.; halogen such as chloro and bromo; alkoxycarbonyl of from 2 to about 8 carbon atoms such as methoxycarbonyl, ethoxycarbonyl, butoxycarbonyl, hexyloxycarbonyl, etc.; carboxyl; cyano; alkenyl of about 2 to 12 carbon atoms such as vinyl, allyl, etc.; formyl; alkanoyl of about 2 to 8 carbon atoms such as acetyl, propionyl, butyryl, hexanoyl, etc.; alkanoylamido of about 2 to 8 carbon atoms such as acetamido, butylamido, etc.; aroylamino such as benzamido; and alkylsulfonamide such as methanesulfonamido, hexanesulfonamido, etc.

Specific examples of the aromatic iodide reactants include iodobenzene, 1,3- and 1,4-diiodobenzene, 1,3,5-triiodobenzene, 4-iodotoluene, 4-iodophenol, 4-iodoanisole, 4-iodoacetophenone, 4,4'-diiodobiphenyl, 4-chloroiodobenzene, 3-bromoiodobenzene, and 2,6- and 2,7-diiodonaphthalene. Our process is particularly useful for the preparation of benzenedicarboxylic and naphthalenedicarboxylic esters with low acid content and thus the preferred reactants are diiodobenzenes, especially 1,3- and 1,4-diiodobenzene, and diiodonaphthalenes, especially 2,6- and 2,7-diiodonaphthalene.

The aromatic iodide reactants are known compounds and/or can be prepared according to published procedures. For example, T. Hudlicky, et al., *The Chemistry of Halides, Pseudohalides and Azides,* Supplement D, Part 2, 1142–1158, the disclosure of which is incorporated herein by reference in its entirety, discloses a number of such processes. Another process described in J. Chem. Soc. 150 (1952) comprises treating an aromatic compound, such as benzene, with iodine in the presence of silver sulfate dissolved in concentrated sulfuric acid.

The ether used in the process of this invention, which is preferably dimethyl ether, results in the formation of methyl carboxylate esters, which may be used in transesterification reactions, and produces methyl iodide which is the most volatile of the alkyl iodides. However, other ethers containing up to about 12 carbon atoms, preferably up to about 4 carbon atoms, may be employed if desired. Examples of other suitable ethers include diethyl ether, dipropyl ether, dibutyl ether, dipentyl ether, dihexyl ether, diheptyl ether, dioctyl ether, didecyl ether, dibenzyl ether, dioxane, anisole, or mixed dialkyl ethers. Mixture of these ethers may also be employed. For each mole equivalent of aromatic ester produced, one mole of ether is required.

The process provided by our invention can also be carried out in the presence of an organic co-solvent such as aliphatic, alicyclic and aromatic hydrocarbons, and halogenated hydrocarbons. Examples of such solvents include benzene, toluene, naphthalene, the xylenes, hexane, heptane, chlorobenzene, ethylene dichloride, methylchloroform, etc. However, the use of a co-solvent is not critical to the practice of this invention. Water or potential esterifying agents such as alcohols and their carboxylate esters may also be present in the reaction mixture depending upon the desired ester to acid ratio.

The palladium catalyst can be provided to the reaction medium as either palladium metal or as any of a number of palladium salts or complexes, such as palladium acetate. The amount of palladium is not significant as long as enough is present to catalyze the reaction. Preferably, the catalyst is present in a concentration of 1 to 0.0001 mole percent, preferably 0.025 to 0.001 mole percent, based on the moles of aromatic iodide reactant. Therefore, the total reaction medium has a catalyst concentration of about 1,000 ppm to 0.1 ppm with preferred catalyst concentrations of 250 to 1 ppm.

The carbonylation reaction is conducted in the presence of carbon monoxide, which is employed in amounts such that the total reaction pressure is suitable for the formation of both the aromatic carboxylic ester and the alkyl iodide. The carbon monoxide employed may be essentially pure or it may contain other gases such as carbon dioxide, hydrogen, methane and other compounds produced by synthesis gas plants. Normally, the carbon monoxide will be at least 90, preferably at least 95, percent pure.

The process of the present invention can be conducted at temperatures and pressures suitable for formation of both the aromatic carboxylic ester and alkyl iodide. The temperatures and pressures are interdependent and can vary considerably. Normally, the pressure will be at least 100 psig. While the process can be carried out at pressures as high as 10,000 psig, the cost of utilities and equipment required for such high pressure operation may not be commercially justified. Thus, the pressure normally will be in the range of about 125 to 10,000 psig, preferably about 300 to 1,500 psig. A more preferred pressure is 500 to 1,500 psig. A pressure of 1,200 psig gives particularly desirable results. While temperatures as low as 125° C. and higher than 225° C. may be used, our process normally is carried out between about 150° to 275° C. The preferred temperature range is 180° to 250° C. A temperature of 220° C. gives particularly desirable results.

The relative amounts of carbon monoxide and ether used in our process can be varied substantially and are, in general, not critical. However, it is preferable to have at least stoichiometric amounts present relative to the aromatic iodide if complete conversion is desired.

When a polyiodo aromatic compound is used as the reactant in our carbonylation process, the products obtained include both aromatic polycarboxylic esters and partially carbonylated products such as iodo aromatic carboxylic esters. The latter compounds are useful as intermediates in the preparation of derivatives of aromatic carboxylic esters, for example, by displacement reactions whereby the iodo substituent is replaced with other radicals. The difunctional esters, such as dimethyl 2,6-naphthalene dicarboxylate, can be reacted with diols to produce high molecular weight polyesters suitable for molding plastics. Useful articles can be molded from these plastics, such as by injection molding. The relative amounts of partially or totally carbonylated products is highly dependent on the period of time that the reactant resides under carbonylation conditions.

The alkyl iodides prepared according to the process of our invention may be used in other chemical processes such as in the preparation of carboxylic acids and carboxylic anhydrides according to known carbonylation procedures. Alternatively, the alkyl iodide can be oxidatively decomposed at elevated temperature to produce a gaseous mixture of iodine, carbon dioxide and water from which the iodine can be recovered. Alternatively, the alkyl iodides may be thermally decomposed to iodine and an alkane, or hydrogenated to hydrogen iodide and methane.

Our process is carried out at a pKa of less than 5. Therefore, there are no significant amounts of basic materials which preferentially combine with hydrogen iodide and interfere with the formation of an alkyl iodide. Examples of such bases which are not present in significant amounts in our process include amines, particularly tertiary amines, and hydroxides, alkoxides and weak acid salts, e.g. carboxylates, of the alkali and alkaline earth metals.

Our invention is further illustrated by the following examples. In the procedures utilized in the examples, the materials employed are loaded into a 330 mL autoclave constructed of Hastelloy B2 alloy which is designed to operate in a rocking mode. The autoclave is pressurized with 200 psig carbon monoxide gas pressure at room temperature and then the gas is vented and the autoclave is sealed. In these examples the autoclave is pressurized to 300 psig with carbon monoxide gas at ambient temperature and heated and rocked until reaction temperature was reached, at which time additional carbon monoxide gas is added to increase the autoclave internal pressure to the predetermined value. Reactor pressure is maintained by adding carbon monoxide at the same rate at which it is consumed by the reactants. The carbon monoxide used is essentially pure. When the predetermined reaction time is completed the autoclave is cooled by a stream of cold air to approximately 25° C. After the gas is vented from the autoclave the crude product is isolated by filtration and analyzed by gas chromatographic methods. The percent conversion is the mole percent of iodo-group converted to carboxylic ester and acid. The results of these runs are shown on the following pages.

| Example No. | 1 | 2 | 3 | 4 | 5 |
|---|---|---|---|---|---|
| Iodoaromatic | 2,6-Diiodonaphthalene | 2,6-Diiodonaphthalene | 2,6-Diiodonaphthalene | 2,6-Diiodonaphthalene | 2,6-Diiodonaphthalene |
| Wt (g) | 30.0 | 30.0 | 30.0 | 30.0 | 30.0 |
| Catalyst | $Pd_3(OAc)_6$ | $Pd_3(OAc)_6$ | $Pd_3(OAc)_6$ | $Pd_3(OAc)_6$ | $Pd_3(OAc)_6$ |

-continued

| Wt (g) | 0.02 | 0.01 | 0.01 | 0.01 | 0.01 |
|---|---|---|---|---|---|
| Ether | Dimethyl Ether | Dimethyl Ether | Dimethyl Ether | Dimethyl Ether | Dimethyl Ether |
| Vol (mL) | 40.0 | 40.0 | 40.0 | 40.0 | 40.0 |
| Other | Methanol | | | | |
| Wt (g) | 5.0 | | | | |
| Co-Solvent | Naphthalene | Naphthalene | Naphthalene | Naphthalene | Naphthalene |
| Wt (g) | 100.0 | 100.0 | 100.0 | 100.0 | 100.0 |
| Time (hour) | 2 | 1 | 1 | 1 | 1 |
| Pressure (psig) | 1,500 | 1,500 | 1,500 | 1,600 | 900 |
| Temp. (°C.) | 220 | 190 | 220 | 240 | 220 |
| % Conversion | 100 | 68.4 | 100.0 | 86.8 | 62.3 |

| Example No. | 6 | 7 | 8 | 9 | 10 |
|---|---|---|---|---|---|
| Iodoaromatic | 2,6-Diiodonaphthalene | 2,6-Diiodonaphthalene | 2,6-Diiodonaphthalene | 2,6-Diiodonaphthalene | 2,6-Diiodonaphthalene |
| Wt (g) | 30.0 | 30.0 | 30.0 | 30.0 | 30.0 |
| Catalyst | $Pd_3(OAc)_6$ | $Pd_3(OAc)_6$ | $Pd_3(OAc)_6$ | $Pd_3(OAc)_6$ | $Pd_3(OAc)_6$ |
| Wt (g) | 0.01 | 0.01 | 0.01 | 0.01 | 0.01 |
| Ether | Dimethyl Ether | Dimethyl Ether | Diethyl Ether | Anisole | Dimethyl Ether |
| Vol (mL) | 40.0 | 40.0 | 40.0 | 40.0 | 40.0 |
| Co-Solvent | Naphthalene | Naphthalene | 1-Methylnaphthalene | 1-Methylnaphthalene | p-Xylene |
| Wt (g) | 100.0 | 100.0 | 100.6 | 100.0 | 84.5 |
| Time (hour) | 1 | 1 | 1 | 1 | 1 |
| Pressure (psig) | 1,000 | 1,200 | 1,500 | 1,500 | 1,200 |
| Temp. (°C.) | 220 | 220 | 220 | 220 | 220 |
| % Conversion | 78.2 | 100.0 | 52.6 | 20.3 | 82.6 |

While the invention has been described in detail with particular reference to preferred embodiments thereof, it will be understood that variations and modifications can be effected within the spirit and scope of the invention.

We claim:

1. A process for the co-production of an aromatic carboxylic ester and an alkyl iodide which comprises carbonylating an aromatic iodide in the presence of an ether and a catalytic amount of a palladium catalyst under aromatic carboxylic ester and alkyl iodide-forming conditions of temperature and pressure.

2. The process of claim 1 wherein the aromatic iodide is selected from the group consisting of diiodonaphthalene and diiodobenzene.

3. The process of claim 2 wherein the diiodonaphthalene is 2,6-diiodonaphthalene and the diiodobenzene is 1,4-diiodobenzene.

4. The process of claim 1 wherein the ether contains from 1 to 4 carbon atoms.

5. The process of claim 4 wherein the ether is dimethyl ether.

6. The process of claim 1 wherein the temperature is in the range of about 150° to 275° C.

7. The process of claim 6 wherein the temperature is in the range of about 180° to 250° C.

8. The process of claim 1 wherein the pressure is in the range of 125 to 10,000 psig.

9. The process of claim 8 wherein the pressure is in the range of 300 to 1,500 psig.

10. The process of claim 1 wherein the process is carried out in the presence of an organic co-solvent.

11. A process of the co-production of an aromatic dicarboxylic ester selected from the group consisting of a dimethyl benzenedicarboxylate and dimethyl naphthalenedicarboxylate and methyl iodide which comprises carbonylating a diiodobenzene or a diiodonaphthalene in the presence of dimethyl either, an organic solvent and a catalytic amount of a palladium catalyst at a temperature of about 190° to 250° C. and a pressure of about 500 to 1,500 psig.

12. A process for the co-production of dimethyl 2,6-naphthalenedicarboxylate and methyl iodide which comprises carbonylating 2,6-diiodonaphthalene in the presence of dimethyl ether, an organic co-solvent and a catalytic amount of palladium at a temperature of about 220° C. and a pressure of about 1,200 psig.

* * * * *